(12) United States Patent
Oborny et al.

(10) Patent No.: US 7,399,449 B1
(45) Date of Patent: Jul. 15, 2008

(54) MICROFABRICATED DIFFUSION SOURCE

(75) Inventors: Michael C. Oborny, Albuquerque, NM (US); Gregory C. Frye-Mason, Cedar Crest, NM (US); Ronald P. Manginell, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 766 days.

(21) Appl. No.: 10/436,595

(22) Filed: May 12, 2003

Related U.S. Application Data (60) Provisional application No. 60/378,035, filed on May 14, 2002.

(51) Int. Cl.
*B01L 3/00* (2006.01)
(52) U.S. Cl. ............................ 422/102; 422/69; 422/88; 96/108; 96/121
(58) Field of Classification Search .................. 422/69, 422/88, 89, 90, 101, 102; 96/101, 102, 108, 96/111, 112, 121, 126, 130
See application file for complete search history.

(56) References Cited

U.S. PATENT DOCUMENTS

| | | | | |
|---|---|---|---|---|
| 5,262,127 A | * | 11/1993 | Wise et al. ..................... 422/98 |
| 5,922,591 A | * | 7/1999 | Anderson et al. ......... 435/287.2 |
| 6,004,450 A | | 12/1999 | Northrup et al. | |
| 6,074,827 A | * | 6/2000 | Nelson et al. ................... 435/6 |
| 6,143,247 A | * | 11/2000 | Sheppard et al. .............. 422/63 |
| 6,171,378 B1 | * | 1/2001 | Manginell et al. ............. 96/143 |
| 6,322,683 B1 | * | 11/2001 | Wolk et al. ................... 204/600 |
| 6,527,835 B1 | * | 3/2003 | Manginell et al. ............. 96/102 |

| | | | | |
|---|---|---|---|---|
| 7,000,452 B2 | * | 2/2006 | Bonne et al. ................ 73/23.25 |
| 7,078,237 B1 | * | 7/2006 | Mowry et al. ................ 436/147 |
| 7,104,112 B2 | * | 9/2006 | Bonne ........................ 73/23.25 |

OTHER PUBLICATIONS

Madou, "MEMS Fabrication," *The MEMS Handbook*, CRC Press, Mohamed Gadel-Hak, ed., pp. 16-66 to 16-71 (2001).
Christophersen et al., "Crystal orientation and electrolyte dependence for micropore nucleation and stable growth on p-type Si," *Mat. Sci. and Eng. B69-70*, 194 (2000).
Chao et al., "Formation of High Aspect Ratio Macropore Array on p-Type Silicon," *Electrochem. & Solid-State Letters* 3(10), 489 (2000).
Altshuller et al., "Application of Diffusion Cells to the Production of Known Concentrations of Gaseous Hydrocarbons," *Analytical Chemistry* 32(7), 803 (1960).
Barratt, "The Preparation of Standard Gas Mixtures," *The Analyst* 106, 817 (1981).
Debbrecht et al., "Diffusion Tubes as a Primary Standard for OSHA-Type Calibration," *Trace Organic Analysis: A New Frontier in Analytical Chemistry*, 716 (1979).
Namiesnik, "Generation of Standard Gas Mixtures," *J. Chromatography* 300, 79 (1984).

\* cited by examiner

*Primary Examiner*—Jill Warden
*Assistant Examiner*—Dwayne K Handy
(74) *Attorney, Agent, or Firm*—Kevin W. Bieg (57) ABSTRACT

A microfabricated diffusion source to provide for a controlled diffusion rate of a vapor comprises a porous reservoir formed in a substrate that can be filled with a liquid, a headspace cavity for evaporation of the vapor therein, a diffusion channel to provide a controlled diffusion of the vapor, and an outlet to release the vapor into a gas stream. The microfabricated diffusion source can provide a calibration standard for a microanalytical system. The microanalytical system with an integral diffusion source can be fabricated with microelectromechanical systems technologies.

12 Claims, 5 Drawing Sheets

MICROFABRICATED DIFFUSION SOURCE

CROSS-REFERENCE TO RELATED APPLICATION

This application claims the benefit of U.S. Provisional Application No. 60/378,035, filed on May 14, 2002.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to diffusion sources and, more particularly, to a microfabricated diffusion source that can provide precise gas or vapor standards for microanalytical systems.

BACKGROUND OF THE INVENTION

For a wide array of analytical techniques, accurate analysis of air or other gas contaminants requires the generation of standard atmospheres to calibrate and verify instrument response. Direct injection of a standard atmosphere into an analytical system can also be used as a diagnostic tool to evaluate the performance of individual system components and the overall system as a whole. This real-time diagnostic information can then be used to compensate for changes in instrument response due to changes in the operating environment or the deterioration of system components.

Portable, handheld microanalytical systems, which have been termed "chemical laboratories on a chip," are being developed to enable the rapid and sensitive detection of particular chemicals, including pollutants, high explosives, and chemical and biological warfare agents. These microanalytical systems should provide a high chemical selectivity, to discriminate against potential interferents, and the ability to perform the chemical analysis on a short time scale. These microanalytical systems also require accurate, reliable, and field-portable standards for calibration and evaluation of instrument response.

A common analytical technique, particularly for microanalytical systems, is gas chromatography. A conventional gas chromatograph comprises a means for injection of a sample to be analyzed, a supply of carrier gas, a column for separating the components of the sample, and a detector for detecting the separated components that are eluted from the column. For quantitative analysis, it is necessary to accurately determine how much of a component is in the unknown sample. Generally, quantitative analysis requires the comparison of the size of the chromatographic peak of a component in an unknown sample to a chromatographic peak of the same component in a known calibration standard.

In addition to calibration, standards can be used to evaluate quantitative errors in the chromatographic process. Quantitative errors can be associated with peak size measurement, standardization, sampling techniques and sample introduction, and chromatographic system errors. In particular, standards can be used to identify column-induced changes in the sample character and detector errors due to overload or other factors. For example, a standard can be used to determine and correct for retention time shifts due to adsorption or other problems during gas chromatography measurements.

Both static and dynamic methods have been used to produce gas or vapor standards. Dynamic methods, based on continuous flow of a standard-containing gas mixture, have the advantages of reducing adsorption problems and being able to vary the concentration of the standard by simple change in the diluent flow. In general, the standard should be as close to the unknown sample as possible, stable, and of high purity. Especially with trace analysis, sample size of the standard and the unknown sample should be kept the same within measurement error.

One dynamic method to generate vapor standards is to use the diffusion of vapor through a capillary to add small amounts of the vapor to a flowing gas stream. In a conventional diffusion source, the liquid whose vapor is to provide the standard of interest is contained in a reservoir at a known temperature. The liquid is allowed to evaporate from the reservoir and the vapor diffuses through the capillary into a flowing diluent gas stream. The vapor concentration in the resulting gas mixture can then be determined from rate of diffusion of the vapor through the capillary and the flow-rate of the diluent gas.

Whereas such diffusion tubes are well developed for conventional systems, a need exists for accurate, reliable, and field-portable standards for the calibration and evaluation of microanalytical systems. The present invention comprises a microfabricated diffusion source for use with such microanalytical systems. The invention can provide a very small sized calibration source that can be integrated with the fabrication of the microanalytical system by microelectromechanical systems (MEMS) technologies. This integrated fabrication eliminates the need for an external calibration source and also takes advantage of the economies of scale and low cost inherent with MEMS manufacturing. In addition, due to the very low calibrant flux requirements, which are typically in the nanograms or picograms per second, the lifetime of the microfabricated diffusion source can be months to years. These lifetimes can minimize, or in some cases eliminate, the need to periodically replenish the calibration source material.

SUMMARY OF THE INVENTION

The present invention is directed to a microfabricated diffusion source to provide a controlled diffusion rate of a vapor, the source comprising a container comprising a substrate, a porous reservoir formed in the substrate to hold a liquid, a headspace cavity formed in the container in fluidic communication with the porous reservoir to provide an equilibrium vapor of the liquid therein, a diffusion channel formed in the container having an entrance end in fluidic communication with the headspace cavity and an exit end for controlled diffusion of the vapor therethrough, and an outlet formed through a wall of the container at the exit end of the diffusion channel for release of the vapor to a fluid stream. The diffusion source can be fabricated with microelectromechanical systems (MEMS) technologies and materials.

The invention further comprises a method for calibrating a microanalytical system, the method comprising attaching a microfabricated diffusion source to the microanalytical system, injecting the vapor from the microfabricated diffusion source into the microanalytical system, and detecting the vapor after passage through the microanalytical system.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

The present invention comprises a microfabricated diffusion source that can be integrated into a microanalytical system. The microfabricated diffusion source uses the diffusion of vapor from a liquid reservoir through a diffusion channel to add small amounts of the vapor to a flowing diluent gas stream at the sample inlet of the microanalytical system. Furthermore, several diffusion sources of different pure liquids can be placed in the same diluent gas stream to provide multiple vapor standards.

The concentration of the vapor standard in the flowing gas stream can be determined from $$C = RK/F \times 10^6 \quad (1)$$

where C is the vapor standard concentration (ppm), R is the diffusion rate of the vapor (ng/min), K is the reciprocal vapor density of the calibration material (mL/ng), and F is the diluent gas flowrate (mL/min).

The diffusion rate of the vapor through a diffusion channel in the molecular flow regime is given by $$R = 2.216 \times 10^6 (DMPA/TL) \log[P/(P-P_v)] \quad (2)$$

where D is the vapor diffusion coefficient (cm$^2$/sec), M is the vapor molecular weight (g/mol), P is the atmospheric pressure (Torr), A is the diffusion channel cross-section (cm$^2$), T is the source temperature (° K), L is the diffusion channel length (cm), and $P_v$ is the partial pressure of the diffusing vapor (Torr).

The diffusion coefficient depends on the pressure and temperature according to $$D = D_o (T/T_o)^m (P_o/P) \quad (3)$$

where $D_o$ is the diffusion coefficient under normal conditions (i.e., $T_o = 298°$ K and $P_o = 760$ Torr) and m is a constant, generally assumed to be 2.

From these equations, it can be seen that at constant atmospheric pressure the vapor standard concentration can be varied by changing the diluent gas flowrate, diffusion channel cross-section or length, or source temperature. A known and controllable amount of vapor standard can therefore be added to a diluent flowing gas stream by controlling the diffusion channel construction and temperature. In general, the diffusion channel dimensions can be fabricated to provide an optimum range of concentrations for a given standard material. The temperature of the diffusion source and the flow rate of the diluent gas can then be varied to control the concentration within this range. For a source with a diffusion channel of fixed dimension, the diffusion rate is a function of temperature only and will remain uniform at a fixed temperature. Therefore, by varying the operating temperature of the diffusion source, it is possible to change the diffusion rate of the vapor in a known and predictable manner. In general, the temperature must be controlled to within ±0.2° C. to obtain ±1% accuracy in the flow rate of the standard vapor.

The microfabricated diffusion source can further comprise a permeation medium in the diffusion channel for permeation of the vapor therethrough. Such permeation tubes are commonly used in the industry for the generation of low concentration standards at the ppm level of volatile chemicals or pressurized gases. The permeation medium can be a polymer, such as polyethylene, polypropylene, or polytetrafluoroethylene. For a permeation source, R in Eq. (1) is replaced by the permeation rate given by $$R = DS(P_1 - P_2)A/L \quad (4)$$

where D is the diffusion coefficient, S is the solubility coefficient, $P_1$ and $P_2$ are the partial pressures on each side of the permeation medium, A is the permeation medium cross-sectional area, and L is the permeation length of the permeation medium.

Figure 1A:
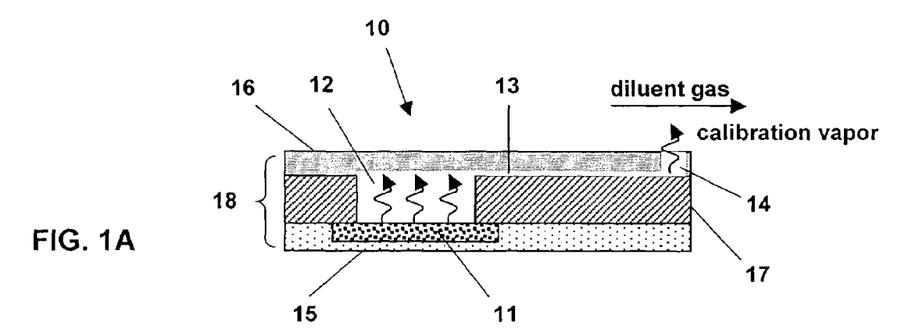
FIGS. 1A-1C show schematic side-view illustrations of different embodiments of a microfabricated diffusion source.
Figure 1B:
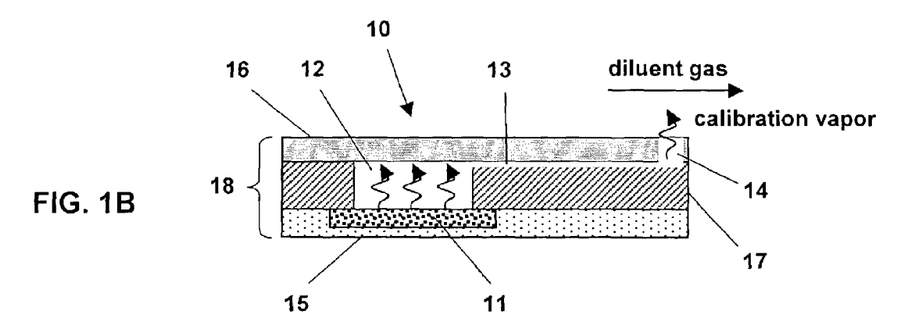
Figure 1C:
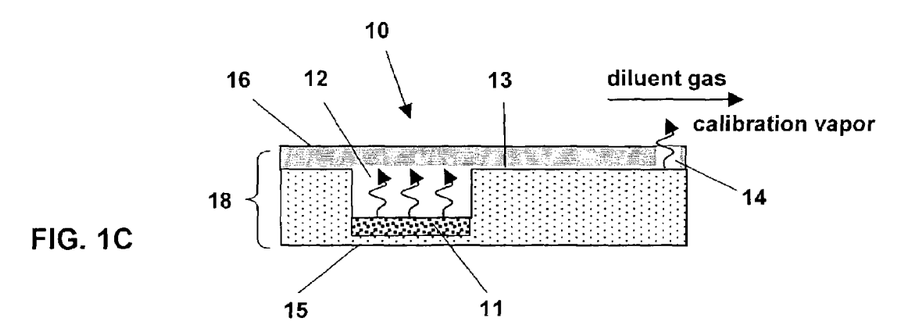

FIGS. 1A-1C show different embodiments of the microfabricated diffusion source 10 according to the present invention. The microfabricated diffusion source 10 comprises a container 18 comprising a substrate 15, a porous reservoir 11 formed in an inner side of the substrate 15 to hold a liquid, a headspace cavity 12 to provide an equilibrium vapor, a diffusion channel 13 to provide a controlled diffusion of the vapor, and an outlet 14 for releasing the vapor at a controlled rate into a diluent gas flowing into a microanalytical system. The porous reservoir 11 immobilizes the liquid and prevents wicking of the liquid into the diffusion channel 13 while still allowing evaporation of the liquid into the headspace cavity 12. The microfabricated diffusion source 10 can further comprise a permeation medium (not shown) in the diffusion channel 13.

The mass transfer rate of the diffusion source 10 is determined by the source temperature and the cross-sectional area and length of the diffusion channel 13, according to Eq. (2). For accurate determination of the diffusion rate, the weight loss of the liquid from the reservoir can be determined gravimetrically over an appropriate period of time. The concentration of the standard can be varied over a wide range by variation of the diluent gas flow rate or by changing the temperature of the diffusion source 10, according to Eq. (1). For accurate generation of dynamic standards, the temperature can be closely controlled (thermostated), for example, by a resistive heating element (not shown) deposited on an outer side of the substrate 15.

Figure 2:
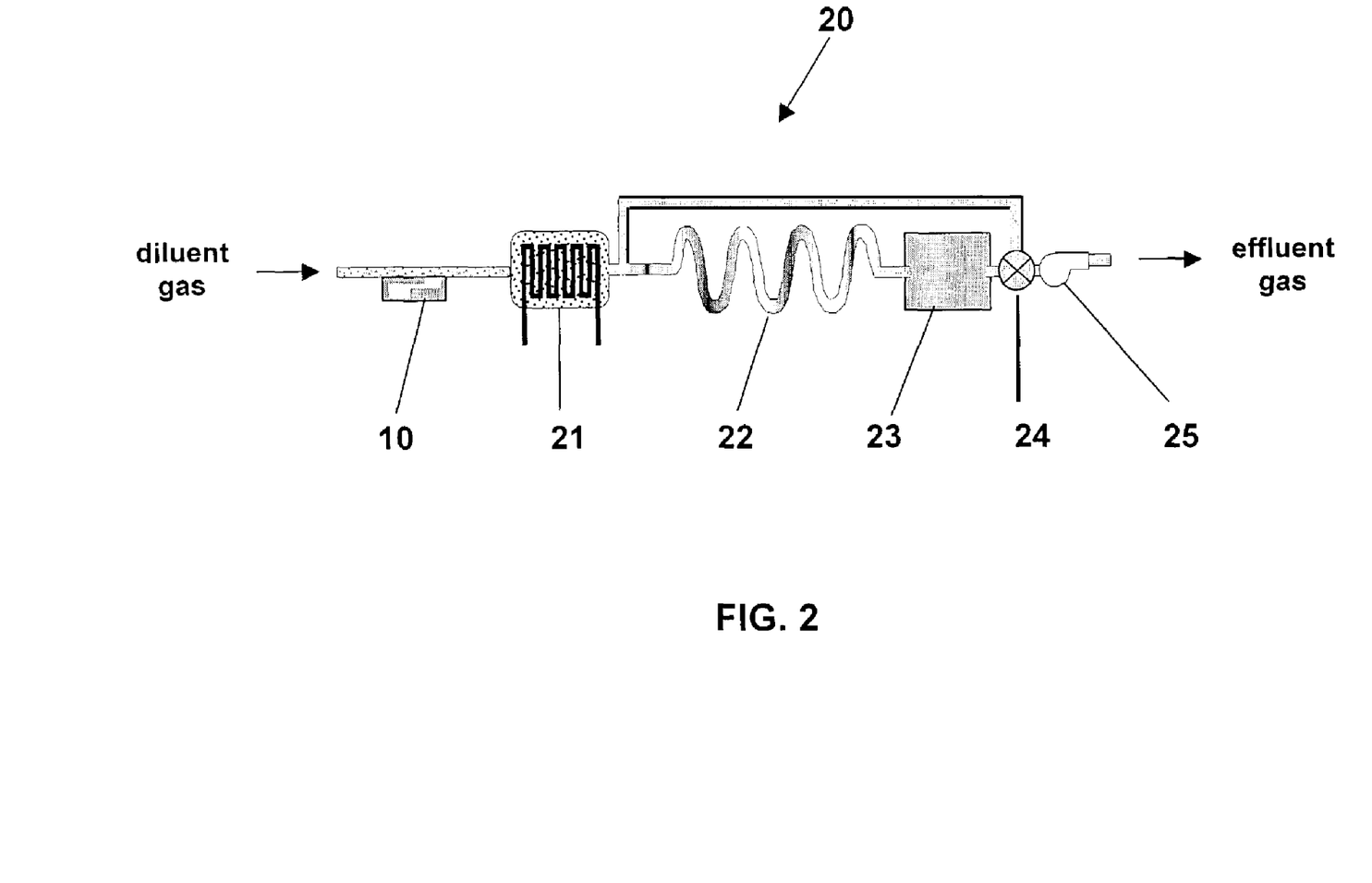
FIG. 2 is a schematic illustration of a microanalytical system comprising the microfabricated diffusion source, a chemical preconcentrator, a gas chromatography column, and a detector.

FIG. 2 shows a typical microanalytical system 20 with a microfabricated diffusion source 10 attached at the sample inlet. The microanalytical system 20 can comprise a chemical preconcentrator 21, to selectively absorb analytes from a gas stream for subsequent pulsed release; a gas chromatography column 22, to chemically separate the released analytes; a chemical detector 23, to analyze the separated analytes; and a bypass valve 24 and pump 25 to control the flow of the sampled atmosphere through the microanalytical system 20. See, e.g., Frye-Mason et al., "Hand-Held Miniature Chemical Analysis System (µChemLab) for Detection of Trace Concentrations of Gas Phase Analytes," *Micro Total Analysis Systems* 2000, 229 (2000).

In a typical system calibration, the diffusion source 10 is placed in a temperature-controlled (thermostat) environment, the calibration liquid retained in the porous reservoir 11 is vaporized into the headspace cavity 12, and the vapor diffuses through the diffusion channel 13 at a known rate (i.e., at a known temperature) to the outlet 14, where the vapor mixes with the diluent gas in the sample inlet to the microanalytical system 20. To generate a standard mixture, several microfabricated diffusion sources 10, each containing a different pure calibration material, can be put in the same gas stream.

The microfabricated diffusion source 10 can be fabricated with MEMS technologies using materials that are compatible with the calibration material and the microanalytical system 20. The microfabrication of the diffusion source 10 can be integrated with the microfabrication of the microanalytical system 20 to provide a standard vapor at the sample inlet to the microanalytical system 20.

As shown in FIG. 1A, in a preferred embodiment of the invention, the container 18 comprises the substrate 15, an intermediate layer 17, and a lid 16. The porous reservoir 11 is formed the substrate 15, the headspace cavity 12 is formed in the intermediate layer 17, and the diffusion channel 13 and outlet 14 are formed in the lid 16.

The substrate 15 has an inner side (i.e., the substrate surface facing the inside of the container 18) and an outer side. The substrate 15 can preferably be a silicon wafer.

The porous reservoir 11 can be formed in the inner side of the substrate 15. The porous reservoir 11 can comprise a sorptive material, such as porous silicon. Preferably, a porous silicon reservoir can be formed by room temperature etching of a reservoir portion of the silicon wafer in hydrofluoric acid (HF). The exposed area of the reservoir 11 can be defined by appropriate masking of the silicon wafer during the etching. The depth of the reservoir 11 can be controlled by the etching rate and etch time. The pores can be coated with a hydrophilic or hydrophobic coating to alter the affinity of the porous reservoir 11 for the calibration liquid.

High-aspect-ratio macropores can be formed by chemical, photochemical, or electrochemical etching of both n-type and p-type single crystal silicon. Recently, very well-defined macropores having radii of several microns and aspect ratios of about 100 have been formed by anodization of p-type silicon. Pore density can be defined and pore growth induced by a regular pattern of pits formed by standard lithography and subsequent pre-etching in aqueous KOH. The pore size, uniformity, and depth can be determined by controlled anodization of the pre-etched pits in an HF-containing electrolyte. Current density, HF concentration, and the presence of a cationic surfactant in the electrolyte have been shown to be important for the formation of uniform, unidirectional macropores. See, e.g., Chao et al., "Formation of High Aspect Ratio Macropore Array on p-Type Silicon," *Electrochem. And Solid-State Letters* 3(10), 489 (2000); Christophersen et al., "Crystal orientation and electrolyte dependence for macropore nucleation and stable growth on p-type Si," *Mat. Sci. and Eng.* B69-70, 194 (2000); and U.S. Pat. No. 6,004,450 to Northrup et al., which are incorporated herein by reference.

An important parameter in the design of the diffusion source 10 is the radius of the pores contained in the porous reservoir 11. The radius of the individual pores should preferably be large enough to prevent significant depression of the vapor pressure above the porous reservoir 11 while being small enough so that the pores absorb and retain the calibration liquid, even when the reservoir 11 is inverted. Furthermore, the pore radius is preferably uniform to provide a stable vapor pressure as the liquid is evaporated from the reservoir 11. The equilibrium vapor pressure of the calibration liquid as a function of the pore radius can be estimated from the Kelvin equation $$RT\ln(P_v/P_{sat}) = 2\gamma V/r \qquad (5)$$

where R is the gas constant (J/Kmol), T is the absolute temperature (° K), $P_v$ is the equilibrium vapor pressure, $P_{sat}$ is the saturation vapor pressure, $\gamma$ is the surface tension of the liquid (N/m), V is the molar volume ($m^3$/mol), and r is the radius (m) of the spherical surface of the liquid in the pore. Estimates of the vapor pressure depression for acetophenone and several other organic liquids indicate that the pore radius of the porous reservoir 11 should preferably be in the range of 1 to 5 microns.

The intermediate layer 17 can have a substrate side and a lid side. The headspace cavity 12 can be formed from the substrate side through to the lid side of the intermediate layer 17 by micromachining techniques to provide for equilibrium evaporation of the vapor therein from the liquid-containing porous reservoir 11. The intermediate layer 17 is preferably glass, such as pyrex glass.

The lid 16 can have an inner side (i.e., the lid surface facing the inside of the container 18) and an outer side. The diffusion channel 13 can be dry-etched in the inner side of the lid 16 through a patterning mask. The lid 16 can also be a silicon wafer. The patterning mask defines the width and the length of the diffusion channel 13. The depth of the diffusion channel 13 can be determined by the etch rate and the etch time. The diffusion channel 13 can include a permeation medium (e.g., a polymer) to provide a permeation channel for high vapor pressure liquids.

The diffusion rate equation, Eq. (2), can be used to estimate the dimensions of the diffusion channel 13. For example, the microfabricated diffusion source 10 can be constructed to provide a 5 to 50 parts-per-billion (ppb) acetophenone standard for an analytical diluent flow rate of 50 sccm at ambient system temperatures of 20 to 50° C., respectively. The diffusion channel 13 for the acetophenone standard can have a cross-section of 7800 $cm^2$ (100 μm width×78 μm depth) and a length of 4.0 mm. The volume of a 50% porous reservoir 11 holding the acetophenone liquid can be 2.45 mL. With this reservoir volume, the estimated source life of the acetophenone standard is greater than 3 years at 20° C. and about 4 months at 50° C.

The outlet 14 can be a through-via etched through the lid 16 from the exit end of the diffusion channel 13 to the outer side of the lid 16 by wet or dry etching. The vapor from the diffusion channel 13 released into the diluent gas stream through the outlet 14.

The assembly process can comprise forming the porous reservoir 11 in the substrate 15, filling the porous reservoir 11 with the calibration liquid, forming the diffusion channel 13 and outlet 14 in the lid 16, forming the headspace cavity 12 in the intermediate layer 17, bonding the lid side of the intermediate layer 17 to the inner side of the lid 16, and then bonding the substrate side of the intermediate layer 17 to the inner side of the substrate 15 to form the sealed container 18. The lid 16, intermediate layer 17, and substrate 15 can be aligned during the bonding to provide an open passage for transport of the vapor from the liquid in the porous reservoir 11 into the headspace cavity 12, through the diffusion channel 13, and out the outlet 14. The bonding process further seals the open passage from atmospheric contaminant gases and other interferents, leaving only the outlet 14 exposed to the diluent gas stream.

When the reservoir 11 is prefilled with the calibration liquid, it is generally preferable to bond the inner side of the lid 16 to the lid side of the intermediate layer 17 with a high-temperature bonding process prior to bonding of the substrate side of the intermediate layer 17 to the inner side of the substrate 15, at a low temperature, to avoid exposure of the liquid-filled reservoir 11 to high temperature. The high-temperature bond can be a fusion bond, if both the lid 16 and the intermediate layer 17 are silicon, or an anodic bond, if the lid 16 or the intermediate layer 17 are glass. For example, a silicon lid can be anodically bonded to a pyrex glass intermediate layer at about 450° C. The lid 16 and intermediate layer 17 can be aligned during bonding so that the headspace cavity 12 adjoins the entrance end of the diffusion channel 13 so that vapor in the headspace cavity 12 will enter the diffusion channel 13. The inner side of the substrate 15 can then be bonded to the substrate side of the intermediate layer 17 with a low temperature polymeric sealant. The polymeric sealant should be relatively impermeable to and not chemically attacked by the calibration material. The substrate 15 and intermediate layer 17 can be aligned during bonding so that the reservoir 12 adjoins the headspace cavity 12 to allow evaporation of the vapor therein. Alternatively, the substrate 15, intermediate layer 17, and lid 16 can be bonded together first and the porous reservoir 11 can be filled later with the calibration liquid through an inlet in the wall of the sealed container 18.

Alternatively, as shown in FIG. 1B, the diffusion channel 13 can be formed in the lid side of the intermediate layer 17 and only the outlet 14 formed in the lid 16. If the porous reservoir 11 is prefilled, the inner side of the lid 16 can then be bonded to the lid side of the intermediate layer 17 with a high temperature bond and the substrate side of the intermediate layer 17 bonded to the inner side of the substrate 15 with a low temperature sealant, as described above.

As shown in FIG. 1C, the headspace cavity 12 and the reservoir 11 can alternatively be formed in the same substrate 15 by forming the headspace cavity 12 in the inner side of the substrate 15 and then etching the porous reservoir 11 into the bottom of the headspace cavity 12. The diffusion channel 13 can be formed in the inner side of the lid 16. The inner side of the substrate 15 can then be bonded to the inner side of the lid 16.

Alternatively, the diffusion channel 13, headspace cavity 12, and porous reservoir 11 can all be formed in the same substrate 15 with an exposed diffusion channel 13 on the inner side of the substrate 15. A lid 16, having only an outlet 14 formed therein, can then be bonded to the inner side of the substrate 15 to provide the sealed container 18. Alternatively, the exposed channel 13 can be sealed against the inlet tube of the microanalytical system 20 to provide a sealed path for the vapor to be transported from the reservoir 11 through the headspace cavity 12 and diffusion channel 13 and into the sample inlet.

A test of the microfabricated diffusion source 10 attached to the sample inlet of the microanalytical system 20 was performed using dimethyl methyl phosphonate (DMMP) as the standard.

The diffusion rate of a vapor from the microfabricated diffusion source can be predicted from the physical properties of the standard material, according to Eq. (2). However, accurate diffusion coefficient and vapor pressure data for DMMP are not readily available. Therefore, the diffusion rate of DMMP vapor was determined experimentally with a conventional diffusion source consisting of a liquid DMMP reservoir and a capillary of known dimensions. The weight loss of DMMP from the conventional diffusion source was measured gravimetrically at several elevated temperatures over extended time periods. The diffusion rate of DMMP from the microfabricated diffusion source at ambient temperature was then estimated by extrapolating the diffusion rate data from these high-temperature measurements to lower temperatures and correcting for the different dimensions of the diffusion channel in the microfabricated diffusion source using Eq. (2).

Figure 3:
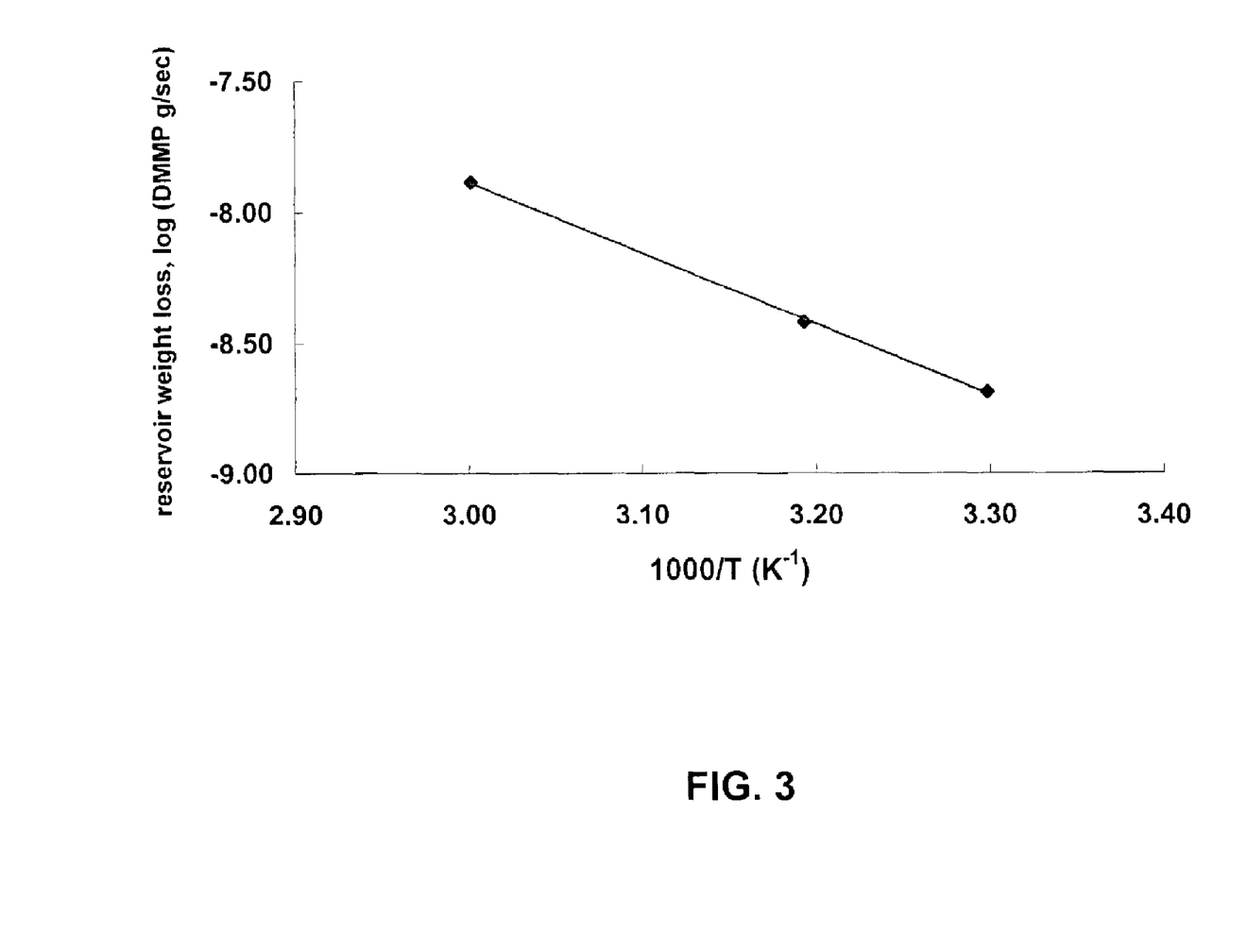
FIG. 3 is a graph of the diffusion rate of dimethyl methyl phosphonate (DMMP) from a diffusion tube as a function of temperature.

In FIG. 3 is shown a graph of the weight loss from the conventional diffusion source as a function of inverse temperature. Weight loss data were taken at reservoir temperatures of 30, 40, and 60° C. for periods of one to several months. The weight loss data exhibited a positive Arrhenius-type temperature dependence, allowing extrapolations to temperatures below 30° C. The weight loss of DMMP from the conventional diffusion source was estimated to be 79.8 ng/min at 24° C. The capillary of the conventional diffusion source had a cross-sectional area of 0.369 mm$^2$ and length of 1.30 cm. The diffusion channel of the microfabricated diffusion source had a cross-section of 0.4 mm$^2$ (1 mm width×400 µm depth) and a length of 1.30 cm. Therefore, correcting for the difference in cross-sectional areas, the predicted diffusion rate of DMMP from the microfabricated diffusion source was 86.5 ng/min at 24° C.

The microfabricated diffusion source was attached to the sample inlet of a microanalytical system, comprising a chemical preconcentrator, a gas chromatography column, and a surface acoustic wave (SAW) detector. The diffusion rate of DMMP from the microfabricated diffusion source was measured by loading the chemical preconcentrator with DMMP vapor released from the microfabricated diffusion source for a sampling period, rapidly heating the preconcentrator to inject a pulse of the sorbed DMMP into the gas chromatography column, and detecting the peak eluted from the gas chromatographic column with the calibrated SAW detector.

Figure 4:
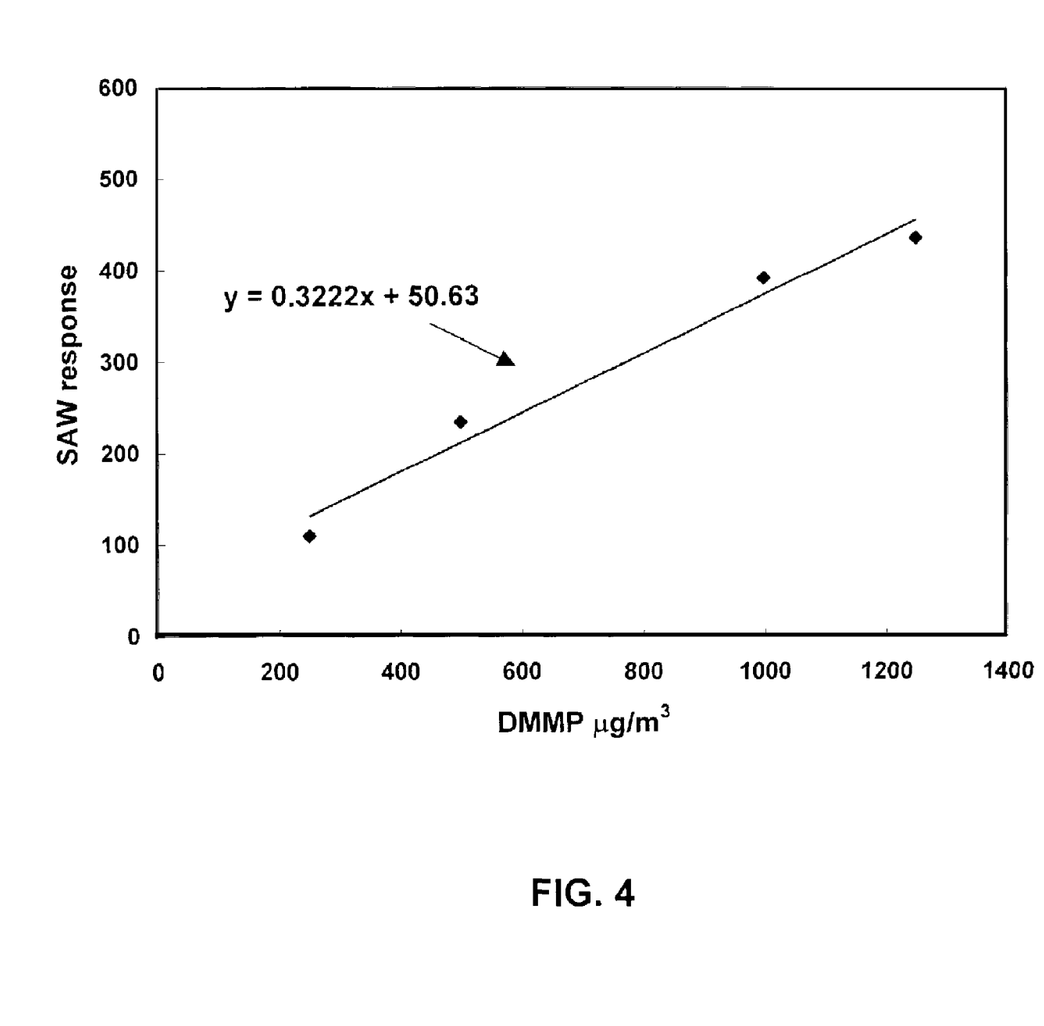
FIG. 4 is a graph of the response of a 2-propyl-[3,5-bis (trifluoromethyl)phenol]-polymethylsiloxane-coated surface acoustic wave (SAW) detector as a function of DMMP concentration.

The SAW detector had a chemically sensitive surface coating of 2-propyl-[3,5-bis(trifluoromethyl)phenol]-polymethylsiloxane and could detect nanogram levels of DMMP. The SAW detector was calibrated by exposing the detector to known concentrations of DMMP. In FIG. 4 is shown the calibrated SAW detector response curve as a function of DMMP concentration.

The porous silicon reservoir of the microfabricated diffusion source was prefilled with liquid DMMP. The diffusion source was allowed to operate at ambient temperature of 24° C., which was monitored to within 1° C. The DMMP from the microfabricated diffusion source was flowed into the chemical preconcentrator with 250 cc/min of diluent air. The preconcentrator was loaded for about one minute to selectively sorb the DMMP. Then the preconcentrator was rapidly heated to 200° C. to release a pulse of the sorbed DMMP in a fraction of a second. The DMMP pulse was injected into the gas chromatography column comprising an 86-centimeter-long spiral channel. The DMMP eluted from the gas chromatography column was passed over the SAW detector.

Figure 5:
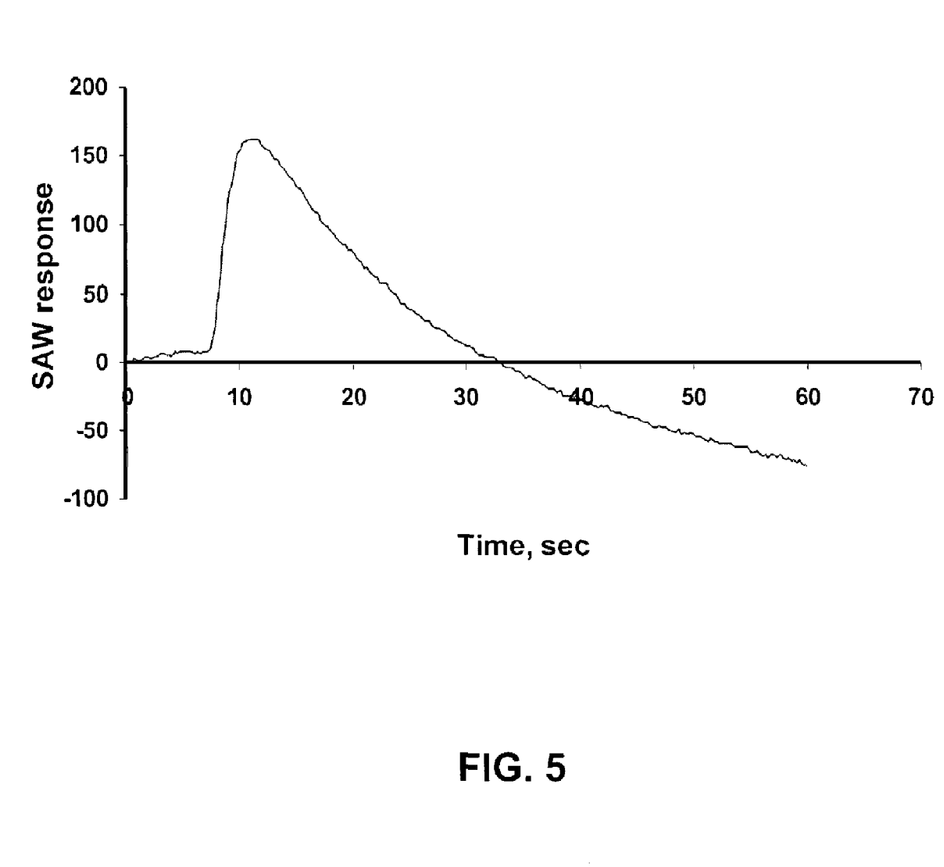
FIG. 5 is a plot of the response of the SAW detector at the end of the gas chromatography column, following the pulsed release of sorbed DMMP from a preconcentrator that was loaded with DMMP from a microfabricated diffusion source.

In FIG. 5 is shown the response of the SAW detector following the pulsed release of sorbed DMMP from the preconcentrator that was loaded with DMMP from the microfabricated diffusion source. The retention time of the DMMP in the gas chromatography column was about 11 seconds, after which the SAW detector recorded a peak due to the eluted DMMP. The size of the chromatographic peak was related to the diffusion rate of the microfabricated diffusion source through the SAW detector response curve. Accordingly, the measured diffusion rate for DMMP was about 83.8 ng/min, in good agreement with the predicted diffusion rate.

These results indicate that the microfabricated diffusion source can be used for the calibration and evaluation of microanalytical systems.

It will be understood that the above description is merely illustrative of the applications of the principles of the present invention, the scope of which is to be determined by the claims viewed in light of the specification. Other variants and modifications of the invention will be apparent to those of skill in the art.

We claim:

1. A microfabricated diffusion source to provide a controlled diffusion rate of a vapor, comprising:
    a substrate having a hollow cavity formed therein,
    a lid bonded to the cavity-side of the substrate to enclose the hollow cavity,
    a porous reservoir formed in the cavity of the substrate to hold a liquid,
    a headspace formed in the cavity in fluidic communication with the porous reservoir to provide an equilibrium vapor of the liquid therein,
    a diffusion channel, having a cross-section, a length, an entrance end in fluidic communication with the headspace and an exit end for controlled diffusion of the vapor therethrough, wherein the cross-section and length are selected so that the diffusion rate of the vapor through the diffusion channel is in the molecular flow regime and wherein the diffusion rate R of the vapor through the diffusion channel in the molecular flow regime is given approximately by $R=2.216\times10^6(DMPA/TL)\log[P/(P-P_v)]$, where D is the vapor diffusion coefficient ($cm^2/sec$), M is the vapor molecular weight (g/mol), P is the atmospheric pressure (Torr), A is the diffusion channel cross-section ($cm^2$), T is the source temperature (°K), L is the diffusion channel length (cm), and $P_v$ is the partial pressure of the diffusing vapor (Torr), and
    an outlet formed through the lid at the exit end of the diffusion channel for release of the vapor to a gas stream.

2. The microfabricated diffusion source of claim 1, further comprising an intermediate layer disposed between the substrate and the lid, wherein the headspace is formed through the intermediate layer.

3. The microfabricated diffusion source of claim 1, wherein the substrate further comprises an inlet for filling of the porous reservoir with the liquid.

4. The microfabricated diffusion source of claim 1, further comprising means for controlling the temperature of the microfabricated diffusion source.

5. The microfabricated diffusion source of claim 4, wherein the temperature controlling means comprises a resistive heating element deposited on the outer side of the substrate.

6. The microfabricated diffusion source of claim 1, wherein the substrate comprises silicon.

7. The microfabricated diffusion source of claim 6, wherein the porous reservoir comprises porous silicon.

8. The microfabricated diffusion source of claim 7, wherein the porous silicon is formed by electrochemical etching in doped single-crystal silicon.

9. The microfabricated diffusion source of claim 1, wherein the porous reservoir has a pore radius of less than 10 microns.

10. The microfabricated diffusion source of claim 1, wherein the diffusion channel is formed in the substrate.

11. The microfabricated diffusion source of claim 1, wherein the diffusion channel is formed in the lid.

12. The microfabricated diffusion source of claim 2, wherein the diffusion channel is formed in the intermediate layer.

* * * * *